(12) United States Patent  
Mohr et al.

(10) Patent No.: US 8,895,289 B2  
(45) Date of Patent: Nov. 25, 2014

(54) METHOD AND DEVICE FOR PHOTOCHEMICAL PROCESS

(75) Inventors: Martin Mohr, Hainburg (AT); Franz Emminger, Hainburg (AT)

(73) Assignee: Ecoduna AG, Hainburg (AT)

( * ) Notice: Subject to any disclaimer, the term of this patent is extended or adjusted under 35 U.S.C. 154(b) by 1079 days.

(21) Appl. No.: 12/865,270

(22) PCT Filed: Jan. 27, 2009

(86) PCT No.: PCT/AT2009/000026  
§ 371 (c)(1),  
(2), (4) Date: Jul. 29, 2010

(87) PCT Pub. No.: WO2009/094680  
PCT Pub. Date: Aug. 6, 2009

(65) Prior Publication Data  
US 2010/0330652 A1    Dec. 30, 2010

(30) Foreign Application Priority Data

Jan. 31, 2008 (AT) ................................. A 152/2008  
Jun. 3, 2008 (AT) ................................. A 889/2008

(51) Int. Cl.  
C12N 1/12    (2006.01)  
C12M 3/02    (2006.01)  
C12M 1/09    (2006.01)  
C12M 1/00    (2006.01)

(52) U.S. Cl.  
CPC ............... *C12M 27/20* (2013.01); *C12M 21/02* (2013.01); *C12M 23/50* (2013.01)  
USPC .................. 435/257.1; 435/292.1; 435/294.1; 435/296.1; 47/1.4

(58) Field of Classification Search  
CPC ...... C12M 21/02; C12M 23/50; C12M 27/20; C12N 1/12; A01G 33/00  
USPC ..................... 435/292.1, 257.1, 296.1; 47/1.4  
See application file for complete search history.

(56) References Cited

U.S. PATENT DOCUMENTS 3,468,057 A * 9/1969 Buisson et al. ............ 435/257.1  
3,768,200 A * 10/1973 Klock ............................. 47/1.4  
(Continued)

FOREIGN PATENT DOCUMENTS

DE    29 51 700    7/1980  
DE    41 39 134    6/1992  
(Continued)

OTHER PUBLICATIONS

Florian Graetz, "Teilautomatische Generierung von Stromlauf—und Fluidplaenen fuer mechatronische Systeme" 2006.

*Primary Examiner* — William H Beisner  
(74) *Attorney, Agent, or Firm* — Greenblum & Bernstein, P.L.C.

(57) ABSTRACT

Photochemical process and device adapted to breed, produce, or hydrocultivate microorganisms. The process includes conveying a reaction medium in a reactor in a meander-shaped way that includes moving the reaction medium along a direction that perpendicularly or inclined at an angle to an imaginary horizontal plane, wherein, during the conveying, the reaction medium moves in the reactor at least once along a first direction defined as one of a top down direction and a direction of gravity, moves in the reactor at least once along a second direction defined as one of a bottom up direction and against the direction of gravity, and moves in the reactor one of freely under atmospheric pressure and while exposed to the atmosphere. The process also includes introducing into and removing from the reactor the reaction medium in a continuous manner.

31 Claims, 9 Drawing Sheets

(56) References Cited

U.S. PATENT DOCUMENTS

| | | | |
|---|---|---|---|
| 5,091,315 A * | 2/1992 | McCarty et al. | 435/290.1 |
| 5,500,112 A * | 3/1996 | McDonald | 210/151 |
| 6,174,720 B1 | 1/2001 | Oxley et al. | |
| 8,033,047 B2 * | 10/2011 | Rasmussen et al. | 47/1.4 |
| 2009/0130704 A1 * | 5/2009 | Gyure | 435/41 |

FOREIGN PATENT DOCUMENTS

| | | |
|---|---|---|
| DE | 41 34 813 | 4/1993 |
| DE | 195 07 149 | 9/1995 |
| DE | 196 11 855 | 8/1997 |
| DE | 196 44 992 | 3/1998 |
| DE | 197 47 994 | 1/1999 |
| EP | 0 738 686 | 10/1996 |
| GB | 2 235 210 | 2/1991 |
| GB | 2 330 589 | 4/1999 |
| JP | 62220183 A * | 9/1987 |
| WO | 98/18903 | 5/1998 |
| WO | 99/15620 | 4/1999 |

* cited by examiner

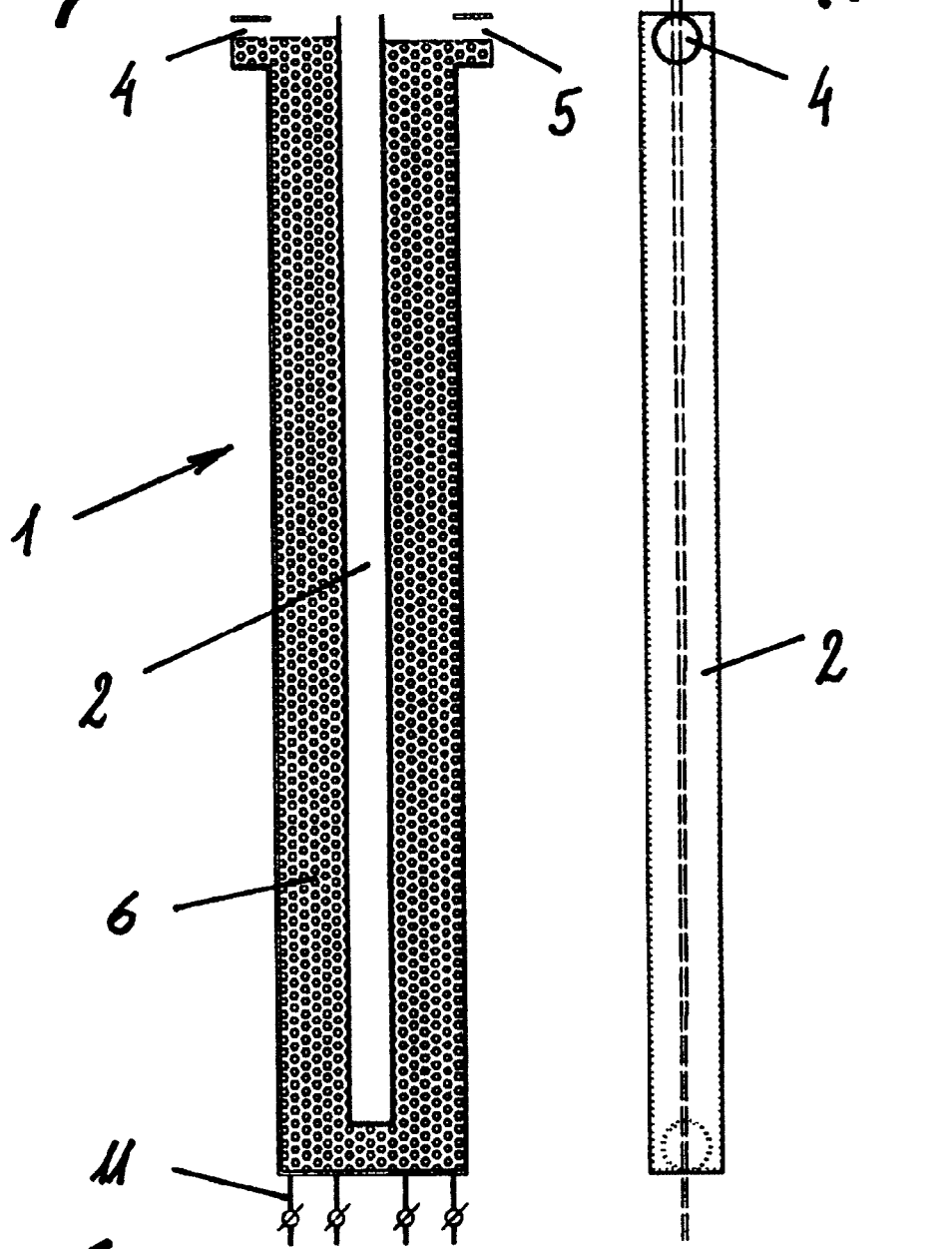
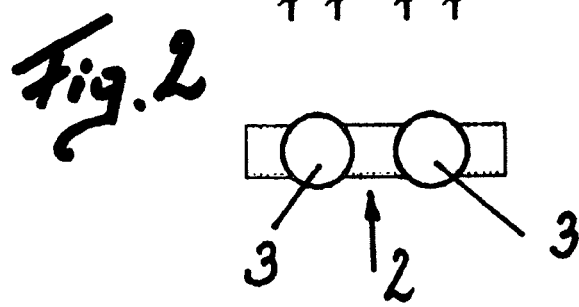

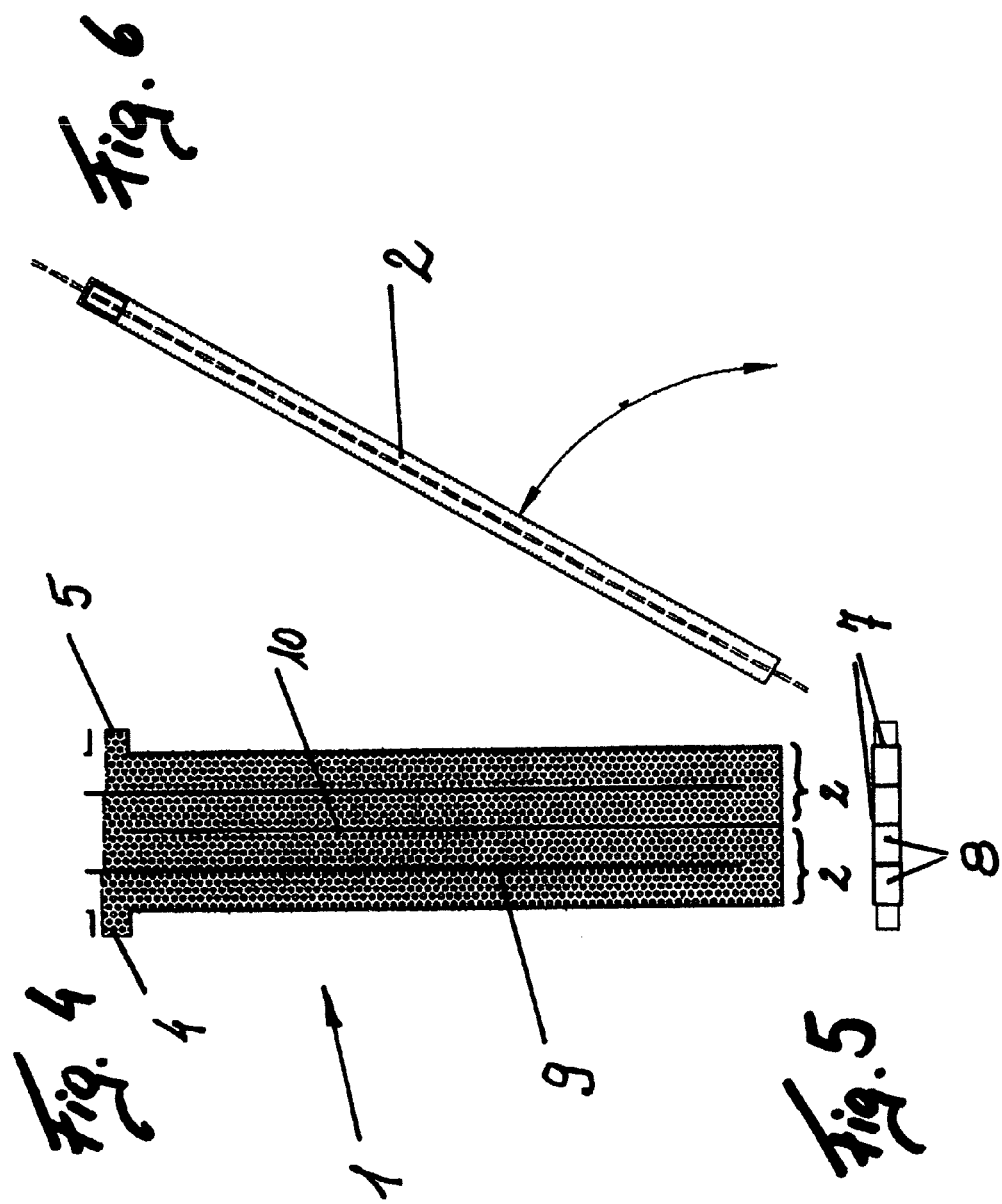

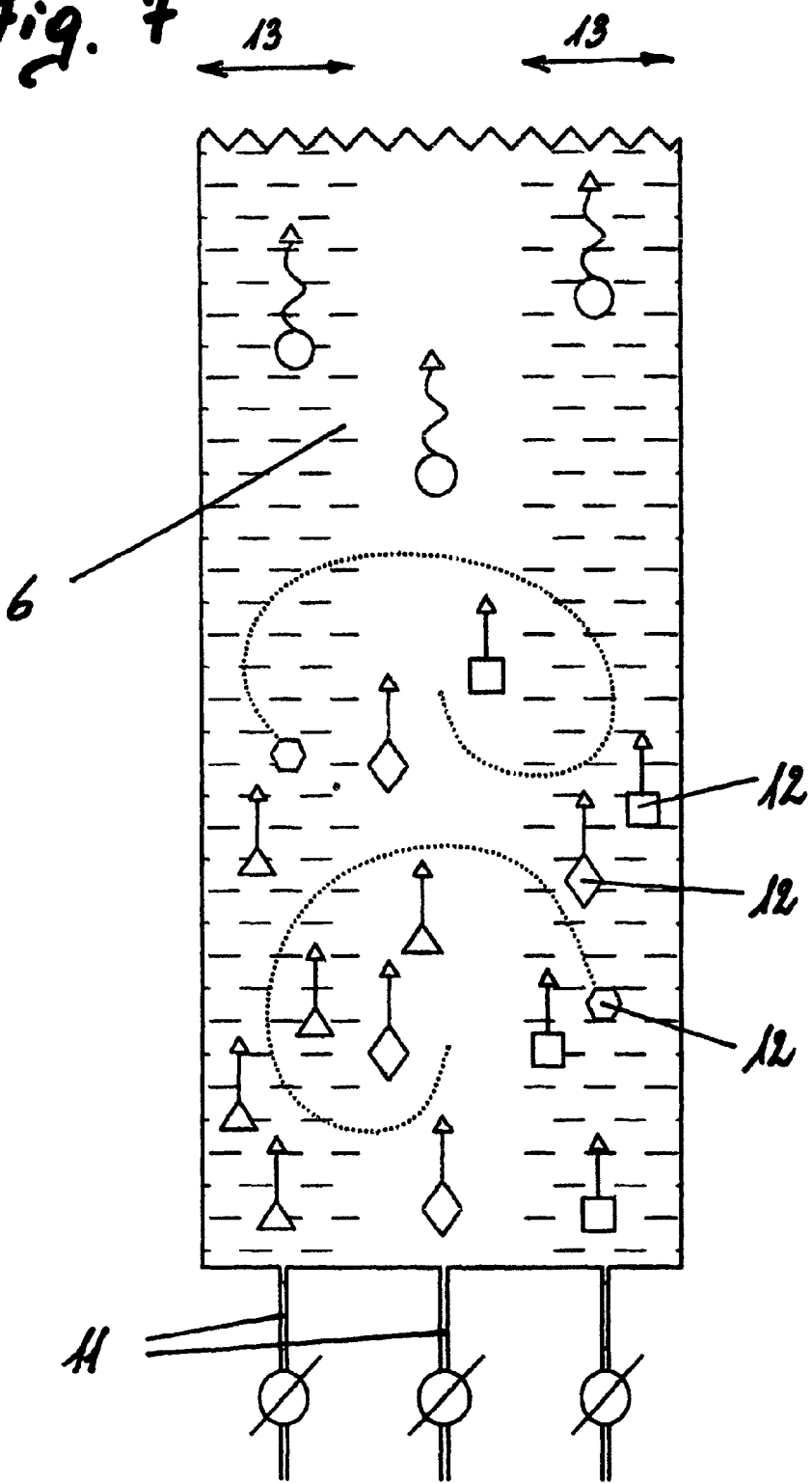

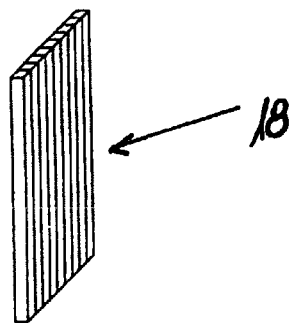
Fig. 13
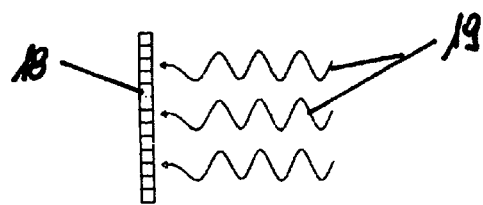
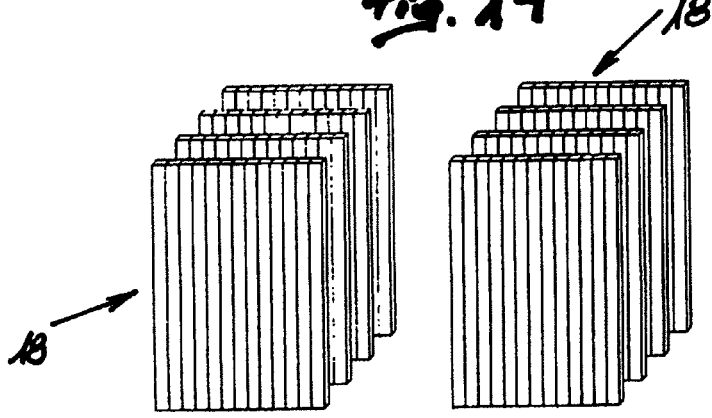
Fig. 14
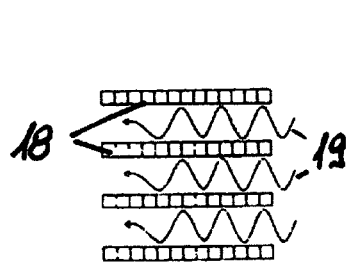
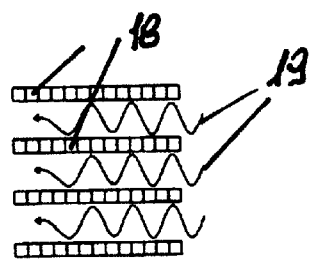

METHOD AND DEVICE FOR PHOTOCHEMICAL PROCESS

CROSS-REFERENCE TO RELATED APPLICATIONS

The present application is a U.S. National Stage of International Patent Application No. PCT/AT2009/000026 filed Jan. 27, 2009 which published as WO 2009/094680 on Aug. 6, 2009, and claims priority of Austrian Patent Application Nos. A 152/2008 filed Jan. 31, 2008 and A 889/2008 filed Jun. 3, 2008.

BACKGROUND OF THE INVENTION

1. Field of the Invention

The invention relates to a photochemical process, such as a photocatalytic and/or photosynthetic process, which can be particularly utilized for the breeding and production or hydrocultivation of preferably phototrophic microorganisms, wherein a reaction medium, for example, an aqueous solution or a suspension, is conducted in a reactor in a meander-shaped way. Furthermore, the invention relates to a device for implementation of the method.

2. Discussion of Background Information

A bioreactor for phototrophic microorganisms, which is made of glass or plastic, is known from DE 41 34 813 A1. The culture medium is either pumped through the bioreactor or conducted towards the bottom in a meander-shaped way through the horizontally positioned web plates. In addition, turbulence-creating media are positioned in the webs. In accordance with this method, carbon dioxide is introduced at the top and natural or artificial light is used to operate. The bioreactor is positioned at a right angle to the light source or tracking it.

Furthermore, bioreactors for phototrophic microorganisms or for photocatalytic processes are also known from GB 2 235 210 A and DE 196 44 992 C1.

Photocatalytic wastewater treatment in a bioreactor is known from EP 738 686 A1, wherein the liquid to be cleaned is conducted through multiple web plates made of transparent plastic. For regulation of the temperature, customary translucent multiple web plates can be used.

Moreover, an actively or passively temperature-controllable solar element made of multiple web plates with at least three belts is described in WO 98/18903. Layers within the reactor are used alternately for a photochemical or photosynthetic process. The culture medium is thereby conducted towards the bottom in a meander-shaped way in a closed reactor with a sealed front and horizontally positioned web plates.

Known are, of course, also the Archimedian screw and the spiral of Da Vinci, for example from Florian Manfred Grätz "Semi-automatic Generation of Circuit and Fluid Diagrams for Mechatronic Systems" (thesis at Munich Tech. Univ. 2006) ISBN 10 3-8316-0643-9.

In addition, a hydropower screw with a trough and a generator for power production is known from DE 195 07 149 C2. A hydropower screw for energy conversion is known from DE 41 39 134 C2.

Naturally, the hydrostatic balance of force is known as hydrostatic paradox, also referred to as Pascal's paradox. This is an apparent paradox which describes the phenomenon that a fluid causes a vertical pressure at the base of a vessel depending on the filling level of the fluid, whereby the shape of the vessel has no influence though.

Vessels which are open at the top and connected at the bottom are called interconnected tanks or interconnected pipes. A homogenous fluid has the same level in these, as the air pressure and gravity have an equal effect on the vessels. In the case of inhomogeneous fluids, the columns of liquid behave inversely to their specific gravity in relation to the level.

Usually, transport in solar reactors is carried out by customary pumping methods, as also in some of the methods mentioned above. This procedure causes stress for the microorganisms in the reaction medium, be it due to high pressure, negative pressure, high acceleration or squeezing. Being subjected to this stress, most of the phototrophic microorganisms relinquish their potential photosynthetic capabilities. Cells are destroyed or damaged and/or the microorganisms need time and/or metabolic products for regeneration before they can fully recuperate the processes assigned them. Equally, most photochemical processes suffer a drop in their potential photocatalytic capabilities under this stress, as molecules are destroyed or damaged and/or require additional time and/or oxidising agents before they can fully recuperate the processes assigned to them.

Furthermore, a solar power plant is known from DE 29 51 700 C2, which is affixed to buildings suspended on an axis of a boom.

SUMMARY OF THE INVENTION

The aim of the invention is to create a method of the type mentioned above, which, on the one hand, avoids the mentioned disadvantages, and, on the other hand, enables a qualitative, and above all, quantitative increase in the yield or harvest.

The method in accordance with the invention is characterised by the fact that the meander-shaped conductance of the reaction medium is carried out perpendicularly or inclined at an angle at least once from the top down or in the direction of gravity, and from the bottom up or against the direction of gravity and that both an introduction and removal of the reaction medium into and from the reactor are preferably carried out continuously, without pressure and freely to the atmosphere via the upper reaction medium surface, wherein due to the hydrostatic pressure compensation and leveling a flow of the reaction medium that is stress-free for the microorganisms is produced. With this invention, it is for the first time possible to achieve a gentle transport for the microorganisms, so that any damage in the course of their production process is prevented. By controlled introduction of the reaction medium in the area of the upper liquid level, the flow rate of the reaction medium through the reactor element can be defined, provided that is filled of course. The reaction medium flows through the perpendicular interconnected reactor elements in a meander-shaped way. The reactor elements are connected with each other in such a way that the inlet and the outlet are positioned at the top. The reactor elements are completely or partially open towards the top. The flow is achieved by utilisation of the hydrostatic pressure compensation with a minimal loss of height within the entire reactor. Due to the largely pressure-free and appression-free transport of the reaction medium in a biosolar reactor, the reaction process is impaired as little as possible.

The method in accordance with the invention can be used, by way of example, for the following areas of use:
  photochemical and/or photosynthetic clarifying of wastewater;
  photosynthetic metabolisation of CO2 into oxygen by phototrophic microorganisms;

breeding and production of phototrophic microorganisms for research purposes;

research on photochemical and/or photosynthetic processes;

breeding and production of phototrophic microorganisms for food products and basic foodstuff materials;

breeding and production of phototrophic microorganisms for basic materials of the pharmaceutical industry;

breeding and production of phototrophic microorganisms for fuels and basic materials for fuel production and power generation;

breeding and production of phototrophic microorganisms for basic materials of the chemical industry; and breeding and production of phototrophic microorganisms which give off exploitable gasses (e.g. hydrogen) within the photosynthetic process.

Stress-free transport of the microorganisms possibly carried along is quasi enabled by making use of the hydrostatic compensation of forces when the reactor medium flows through the reactor elements. In addition, it is possible to achieve an optimisation of energy, defined conductance of light, an optimisation of space, a supply with additives, defined temperature control, targeted regulation, as well as, an improved recovery of gas.

In accordance with another special feature of the invention, a continuous or batch-by-batch introduction of liquid and/or gaseous additives, such as, for example, nutritive solutions and/or oxidising agents and/or active substances and/or dissolved substances promoting the process, is preferably performed during the process and preferably at the bottom side in the area of the diversion of the reactor medium. This way, a controlled and optimised introduction of nutritive solutions and process-promoting solutions, as well as, a controlled and optimised introduction of nutritive and process gasses is enabled. All interventions in the reaction medium are preferably performed at the bottom side of the reaction elements.

In accordance with another embodiment of the invention, the additives are mixed thoroughly and distributed equally in the reaction medium by introducing the additives at the bottom end of the liquid column. This way, a turbulence of the reaction medium is caused by the ascending gasses.

In accordance with a special further development of the invention, the introducable additives are introduced at a defined temperature. This way, a thermal regulation is achieved through the inflowing gasses and/or nutritive solutions.

In accordance with a special feature of the invention, the liquid and/or gaseous substances or additives are introduced at the bottom side in the area of the diversion of the reaction medium, whereby a larger quantity of liquid and/or gaseous substances or additives is introduced in the area of the reaction medium flowing from the bottom up or against the direction of gravity than in the area of the reaction medium flowing from the top down or in the direction of gravity. This way, and in accordance with the operating process of a mammoth pump, the liquid level in the pipe or chamber passed through from the bottom up is raised in comparison with the pipe or chamber passed through from the top down in a kind of "gas lift effect". This difference in the liquid level can lead to a rise of the liquid level at the end of the last pipe or chamber in comparison with the first pipe or chamber in the case of a multiple serial connection of such units and an increased introduction of gas into each ascending pipe, if the rise of the liquid level is taken into account in the design of the reactor. Despite this increased introduction of preferably gaseous additives, a stress-free transport of the microorganisms is enabled.

In accordance with another special feature of the invention, the removal of gaseous process products, such as oxygen, for example, is preferably carried out during the process via the reaction medium surface.

This way, a controlled and optimised reduction of pollutants can be achieved, whereby this optimised removal also permits a recovery of gaseous process products.

In accordance with a special further development of the invention, the reactor is guided or controlled in a revolving manner across the entire arch of the horizontal solar path in conformity with the solar irradiance. This way, an optimisation of the solar irradiance for biosolar reactors is achieved. As a result, phototrophic microorganisms for the most varying applications in different biosolar reactors are provided with optimised natural lighting for the photosynthetic process that is appropriate in terms of nature and the desired breeding success. In addition, this can be adjusted during the day and/or to the changing light conditions. Both an increased as well as a reduced exposition of the microorganisms to the solar irradiance can be achieved, either for better use of the light or for protection against too intensive radiation.

Furthermore, it is also an object of the invention to provide a device for implementation of the method.

The device for implementation of the method in accordance with the invention, utilizes a reactor, in particular, a bioreactor comprising pipes, that is characterised by the fact that the reactor utilizes at least one reactor element, which is formed by two perpendicular pipes connected at the bottom, and that both an inlet and an outlet are provided at the upper reactor edge.

An alternative device for implementation of the method in accordance with the invention, utilizes a reactor, in particular, a bioreactor with elements made of web plates or multiple web plates, that is characterised by the fact that the reactor utilizes at least one reactor element, which is formed by two preferably rectangular, perpendicular chambers formed by the web plates or multiple web plates, which is formed a dividing wall that is open at the bottom, and that both an inlet and an outlet are provided at the upper reactor edge.

The reactor, in particular the bioreactor, can be made of transparent, translucent, coated and uncoated materials. Equally, the pipes or web plates could be made of glass or plastic transparent to light or UV light, such as e.g. polymethylmethacrylate. The reactor elements could be constructed from customary and possibly machined as well as specially manufactured components which meet the requirements noted above.

The reactor elements are arranged in such a way that a continuous, meander-shaped flow from the top down and from the bottom up is ensured. The inlet to and outlet from the reactor are provided in the upper area.

Due to the hydrostatic balance of force, the reaction medium flows through the entire reactor in perpendicular meanders after entering into the reactor. Once it has reached the last reactor element, the reaction medium exits the hydrostatic bioreactor and is conducted pressure-free, or without pressure, to a maturation tank or a receptacle or to another reactor.

From the receptacle, the reaction medium can be finished or stored intermediately or subjected to further processing without stress.

In accordance with a special feature of the invention, the dividing wall for a connection of two or more reactor elements into a reactor panel is designed lower than the dividing wall between the pipes or chambers of a reactor element, as a result of which an overflow or interconnected opening is created when the liquid level in the reactor elements is higher than the dividing wall between the reactor elements. A reactor element is designed as an interconnected vessel. By this type of serial connection of reactor elements into reactor panels, the option is provided to create a defined flow path.

It is possible to influence the optimal length of stay within the entire reactor in adaptation to the relevant phototrophic microorganisms or photochemical requirements and in accordance with the process result by the following parameters:
  flow rate;
  cross-section of the reactor elements;
  height of the reactor elements;
  number and condition of non-gaseous substances introduced; condition, number, density and pressure of gasses blown in;
  number of reactor elements connected to meander-shaped conductance;
  possibility to remove waste-gasses;
  process temperatures;
  length of stay and position towards light; and
  length of stay in maturation tanks and/or darkened tanks In an ideal case and if the relevant structural conditions are provided, unique continuous transport of the medium from the inlet to the outlet is possible for the entire process, if necessary.

In accordance with a special embodiment of the invention, the reactor panels preferably connected with each other in series are arranged into a reactor, in parallel to each other and preferably mounted firmly in a frame-like holding device, and the reactor is adjustable in relation to the incident light radiation via at least one preferably vertical axis using a turning device, whereby the reactor is provided, in particular standing, suspended or swimming, on a float. Due to such a holding device and such a bearing, a random angle towards the solar irradiance is possible. An optimisation of light is achieved by a control in accordance with the solar path or tracking of the sun. Thus, for example, a reduced exposition around noon can be implemented for specific applications by turning away or shading.

As phototrophic microorganisms only undergo an optimal photosynthetic process in the zone near to the surface and are detracted from ingestion and division by too much UV radiation, it is an advantage to be conducted to both the outer zone as well as the interior inside of the reactor element.

Too intensive, directly irradiating UV light damages or impairs the growth of the microorganisms and raises the temperature of the reaction medium above the ideal level, which must be cooled again.

Due to the thorough mixing of the reaction medium, all phototrophic microorganisms reach the light-flooded light zone of the reactor element near the outer wall to a sufficient extent.

For photocatalytic oxidation, it is an advantage if all molecules are conducted to the light-flooded light zone of the reactor element near the outer wall inside of the reactor element.

A positioning nearly in parallel to the light source or tracking of the solar irradiance by the reactor will be sufficient in most cases, thus enabling a massively better utilisation of space.

In addition, light irradiated nearly in parallel is reflected partially by the reactor surface and available to the reactor positioned opposite.

In the case of poor solar irradiance, a bad geographical location, or in the case of phototrophic microorganisms or photocatalytic processes particularly in the need of light, the reactor can be positioned towards the light source at a random angle.

In the preferred variant for enabling biosolar reactors to track the sun, these are mounted firmly at the top and, if necessary, at the bottom in the solar element, so that the reactor panels do not change their position towards each other when the solar element tracks the solar irradiance, but the entire solar element is turned. The reactor panels, which can be flat or fitted together in single pipes, transparent, translucent, coated and uncoated, are arranged in such a way that they are suitable for the breeding of microorganisms, either batch-by-batch in culture medium at rest and/or continuously in flowing culture medium.

In accordance with a further development of the invention, a sensor is provided to record the solar path, via which the rotary movement for incident light radiation for the reactor is controlled. The solar path is determined by a suitable sensor and carried over onto the reactor as a synchronous or randomly defined rotary movement. Naturally, the data related to coordinates, time and date could also be used for control.

In accordance with a special further development of the invention, incident light radiation for the reactor is carried out through artificial lighting. The reactor can be built in such a way and manner that it can be supplied with energy and also lighting media that are of advantage for phototrophic microorganisms can be affixed.

In accordance with a special embodiment of the invention, the rotary movements for incident light radiation in a system utilizing multiple reactors are synchronised preferably for all reactors. In a system consisting of multiple reactors, the rotation of all reactors of the entire system can be synchronised in such a way that the reactors located further back in accordance with a basic assembly are not shaded by positioning the reactor panels nearly in parallel to the solar irradiance. This way, an ideal entry of the sun can be ensured.

In accordance with a further development of the invention, at least parts, in particular, outer surfaces, of the reactor panels and/or the reactor are designed reflecting light. This way, the effect of natural or artificial lighting can be increased.

In accordance with another special feature of the invention, at least one introductory inlet is provided at the bottom side of the reactor in the area of the diversion of the reactor medium for continuous or batch-by-batch introduction of additives, such as, for example, nutritive solutions or gasses and/or oxidising agents and/or active substances and/or dissolved substances or gasses promoting the process, preferably performed during the process.

The reaction medium can optionally be enriched with substances dissolved in liquids that meet the needs of the microorganisms or the requirements of the process before entering into the reactor, and/or supplied with fluid nutrients or oxidising agents in the reactor whilst passing through.

The decreasing level of nutrients in the reaction medium caused by steady growth of the microorganisms during the photosynthetic process can be compensated by continuous and/or batch-by-batch introduction of a nutritive solution.

The decreasing efficiency in the reaction medium during the photochemical process caused by steady reaction can also be compensated by continuous and/or batch-by-batch introduction of additional active substances.

For the introduction of fluid nutrients or oxidising agents, a feeding possibility is created at the bottom side of the reactor elements via controllable valves. Due to the meander-shaped conductance of the reaction medium and/or due to the ascending fluid active substances, thorough mixing and distribution is ensured within the entire reactor.

Naturally, gaseous nutrients, oxidising agents or active substances can also be introduced in this way.

The introduced gasses lead to a self-cleaning of the inner reactor surface due to the ascent of the gas bubbles. A withdrawal point for samples to check the process progress is also provided at the bottom of the reactor element.

In accordance with a special feature of the invention, bored holes for the arrangement of a preferably continuous pipe, in particular a gas pipe with micro-boreholes, are provided in the area of the diversion in the reactor element and/or in the reactor panel for the introduction of additives. The bored holes are arranged on the gas pipe in such a way that gassing and mixing of the reactor medium is ensured in each reactor element of the reactor panel.

In accordance with a special embodiment of the invention, the gas pipe is provided with a larger number of micro-boreholes and/or micro-boreholes with a larger diameter in the area of the reaction medium flowing from the bottom up or against the direction of gravity than in the area of the reaction medium flowing from the top down or in the direction of gravity. This way, the aforementioned "gas lift effect" is achieved in terms of technical installations.

In accordance with a further development of the invention, the gas pipe is provided with an outer and/or inner thread at both ends. The gas pipes, for example, are designed in such a way that these can close off with the assembly gastight by means of a union nut. At least one of these union nuts is provided with a connection for a gas line.

In addition, the gas pipe can be provided with a connecting piece via its inner thread, which in turn can be screwed onto another gas pipe.

For replacement, the union nut is screwed off at one side, the connecting piece is attached, and the new gas pipe is attached to the other end of the connecting piece. Using the new gas pipe, the gas pipe to be replaced is pushed through the assembly and simultaneously takes up its position thereby. This way, it is ensured that the gas pipe to be replaced is pushed through the assembly under a minimal loss of gas or loss of liquid using the new gas pipe. This design permits maintenance or modification of the gas inlet unit without operational interruption or only minimal impairment of the process.

In accordance with another special feature of the invention, a removal outlet is provided for the removal of gaseous process products, such as oxygen for example, preferably carried out during the process, and which is provided above the reaction medium surface or above the upper side of the reactor elements. Gaseous process products, such as metabolites, which are formed in the photosynthetic or photochemical process, can ascend freely in the reaction medium due to the pressure-free condition in the reactor element.

As a result of the completely or partially open design of the reactor element towards the top, an escape and/or evacuation of the gaseous process products is enabled.

The removal of waste-gasses is promoted by the ascending bubbles formed in the process and/or controlled by gasses additionally blown in, if required.

In accordance with an embodiment of the invention, a collecting device with a removal outlet provided above the reaction medium surface or above the upper side of the reactor elements is provided for the removal of gaseous process products. As a result, the gaseous process products can be collected and provided for further exploitation or disposal, if required. A loss of reaction medium due to evaporation and/or due to spilling and a controlled discharge and collection of gasses is also enabled by an enclosed type of construction.

In accordance with an advantageous further development of the invention, a siphon is provided before the inlet and/or after the outlet. The inflow to the reactor is placed in the upper area. The reaction medium can be conducted to the first reactor element pressure-free or without pressure and gastight, if required, through a siphon and conducted away without pressure and gastight, if required, through another siphon after the reactor.

In accordance with a special feature of the invention, an Archimedian screw or a spiral of Da Vinci is provided both inside the reactor as well as between reactors for transport of the reaction medium.

In the case of such an arrangement, one or more tubes or webs are rolled up spirally on an axis with single or multiple bearings and mounted robustly using any technical method, such as, for example, screwed, glued, etc. The relevant tubes or webs are open at both ends. The transport element is aligned and supported in such a way that the bottom end of the tubes or webs scoops reaction medium from a receptacle.

However, tubes or webs are dipped only so far into the reaction medium that the tube end or web emerges above the surface outside of the reaction medium at each rotation.

By slow rotation in the direction of the spiral, which does not result in any significant centrifugal forces, the reaction medium in the relevant lower halves of the tubes or webs is transported to the upper end of the screw under utilisation of the hydrostatic pressure compensation. Upon each rotation, the liquid contained in the top half-turn is released and falls into a receptacle that is positioned at a higher level than the original receptacle. By alternatively full or partial closure of the transport device, spilling and/or gas outlet can be prevented.

The invention also relates to a photochemical process adapted to breed, produce, or hydrocultivate microorganisms, wherein the process comprises conveying a reaction medium in a reactor in a meander-shaped way that includes moving the reaction medium along a direction that perpendicularly or inclined at an angle to an imaginary horizontal plane, wherein, during the conveying, the reaction medium: moves in the reactor at least once along a first direction defined as one of a top down direction and a direction of gravity; moves in the reactor at least once along a second direction defined as one of a bottom up direction and against the direction of gravity; and moves in the reactor one of freely under atmospheric pressure and while exposed to the atmosphere. The method also includes introducing into and removing from the reactor the reaction medium is a continuous manner.

An upper surface of the reaction medium in the reactor may be exposed to the atmosphere, and wherein the process produces hydrostatic pressure compensation and a leveling flow of the reaction medium. The photochemical process may be at least one of a photocatalytic process and a photosynthetic process. The microorganisms may comprise phototrophic microorganisms and the reactor is a bioreactor. The reaction medium may be one of an aqueous solution and a suspension.

The photochemical process may further comprise one of: continuously introducing additives into the reaction medium; batch-by-batch introducing additives into the reaction medium; introducing additives to a bottom area of the reactor; and introducing additives to a bottom area of the reactor in a manner which promotes diffusion.

The additives may comprise one of: liquid additives; gaseous additives: nutritive solutions; oxidising agents; active substances; and dissolved substances. The photochemical process may further comprise introducing additives into the reaction medium at a bottom end of a liquid column so that the additives are mixed thoroughly and distributed equally in the reaction medium. The photochemical process may further comprise introducing additives into the reaction medium at a known temperature. The photochemical process may further comprise introducing additives into the reaction medium at a location wherein the reaction medium diverges, wherein a larger quantity of the additives flows along the second direction than the first direction.

The photochemical process may further comprising one of: removing gaseous process products; removing oxygen; and removing gaseous process products from a reaction medium surface.

The photochemical process may further comprise one of: moving the reactor along an arcuate horizontal solar path; guiding the reactor along an arcuate horizontal solar path; controlling a movement of the reactor along an arcuate horizontal solar path; and moving the reactor along an arcuate path that allows the reactor to receive solar irradiance.

The photochemical process may further comprise one of: during the conveying, conveying the reaction medium in pipes of the reactor; and during the conveying, conveying the reaction medium in at least one reactor element comprising two perpendicular pipes connected at a bottom of the reactor, wherein the reactor comprises an inlet and an outlet arranged at an upper end.

The photochemical process may further comprise one of: during the conveying, conveying the reaction medium between web plates of the reactor; and during the conveying, conveying the reaction medium between chambers formed by a dividing wall that is open at a bottom of the reactor, wherein the reactor comprises an inlet and an outlet arranged at an upper end.

The photochemical process may further comprise one of: utilizing one of an overflow and interconnected opening one of: between reactor elements; and at a location higher than a dividing wall between reactor elements.

The photochemical process may further comprise one of connecting reactor panels with each other; connecting reactor panels in series with each other; arranging reactor panels parallel to each other in the reactor; arranging reactor panels in a frame-like holding device; and arranging reactor panels in a frame-like holding device having at least one vertical axis that allows for movement of the reactor in relation to incident light radiation.

The photochemical process may further comprise recording with a sensor a solar path and controlling movement of the reactor. The photochemical process may further comprise exposing the reactor to incident light radiation in the form of artificial light. The photochemical process may further comprise exposing multiple reactors to incident light radiation. The photochemical process may further comprise one of exposing reflective surfaces of the reactor to incident light radiation; and exposing outer surfaces of the reactor to incident light radiation.

The invention also provides for a device for performing the photochemical process of the type described above, wherein the device comprises an arrangement structured and arranged to continuously introduce into and remove from a reactor a reaction medium and a conveying arrangement structured and arranged to convey a reaction medium in the reactor in a meander-shaped way that includes moving the reaction medium along a direction that perpendicularly or inclined at an angle to an imaginary horizontal plane, wherein, during the conveying, the reaction medium moves in the reactor: at least once along a first direction defined as one of a top down direction and a direction of gravity; at least once along a second direction defined as one of a bottom up direction and against the direction of gravity; and one of freely under atmospheric pressure and while exposed to the atmosphere.

The invention also provides for a device for performing the photochemical process, comprising an arrangement structured and arranged to continuously introduce into and remove from a reactor a reaction medium and a conveying arrangement structured and arranged to convey a reaction medium in the reactor in a meander-shaped way that includes moving the reaction medium along a direction that perpendicularly or inclined at an angle to an imaginary horizontal plane, wherein, during the conveying, the reaction medium moves in the reactor: at least once along a first direction defined as one of a top down direction and a direction of gravity; at least once along a second direction defined as one of a bottom up direction and against the direction of gravity; and one of freely under atmospheric pressure and while exposed to the atmosphere.

The device may further comprise a device structured and arranged to one of: continuously introducing additives into the reaction medium; batch-by-batch introducing additives into the reaction medium; introducing additives to a bottom area of the reactor; and introducing additives to a bottom area of the reactor in a manner which promotes diffusion.

The additives may comprise one of: liquid additives; gaseous additives; nutritive solutions; oxidising agents; active substances; and dissolved substances. The device may further comprise a device for introducing additives into the reaction medium at a bottom end of a liquid column so that the additives are mixed thoroughly and distributed equally in the reaction medium. The device may further comprise a device for introducing additives into the reaction medium comprising at least one bored holes, micro-boreholes, inner threads and outer threads. The device may further comprise a pipe for introducing additives into the reaction medium comprising at least one bored holes, micro-boreholes, inner threads and outer threads. The device may further comprise a collecting device for collecting gas having a removal outlet arranged above one of a surface of the reaction medium and an upper side of the reactor. The device may further comprise at least one siphon. The device may further comprise one of an Archimedian screw and a spiral of Da Vinci arranged inside the reactor.

The invention also provides for a photochemical process adapted to breed, produce, or hydrocultivate microorganisms, wherein the process comprises conveying a reaction medium in a reactor in a meander-shaped way that includes: moving the reaction medium in the reactor at least once along a first direction defined as one of a top down direction and a direction of gravity; moving the reaction medium in the reactor at least once along a second direction defined as one of a bottom up direction and against the direction of gravity; and moving the reaction medium in the reactor one of freely under atmospheric pressure and while exposed to the atmosphere, wherein, during the conveying, the microorganisms move in a stress-free manner.

BRIEF DESCRIPTION OF THE DRAWINGS

The invention is explained in more detail on the basis of exemplary embodiments illustrated in the figures wherein:

FIG. 1 shows a bioreactor consisting of pipes;
FIG. 2 shows a top view in accordance with FIG. 1;
FIG. 3 shows a side elevation in accordance with FIG. 1;
FIG. 4 shows a bioreactor consisting of web plates;
FIG. 5 shows a top view in accordance with FIG. 4;
FIG. 6 shows a side elevation in accordance with FIG. 4;
FIG. 7 shows a schematic illustration of a pipe.

FIGS. 13 and 14 show a schematic illustration of the solar irradiance on the bioreactor.

DETAILED DESCRIPTION OF THE INVENTION

Figure 8:
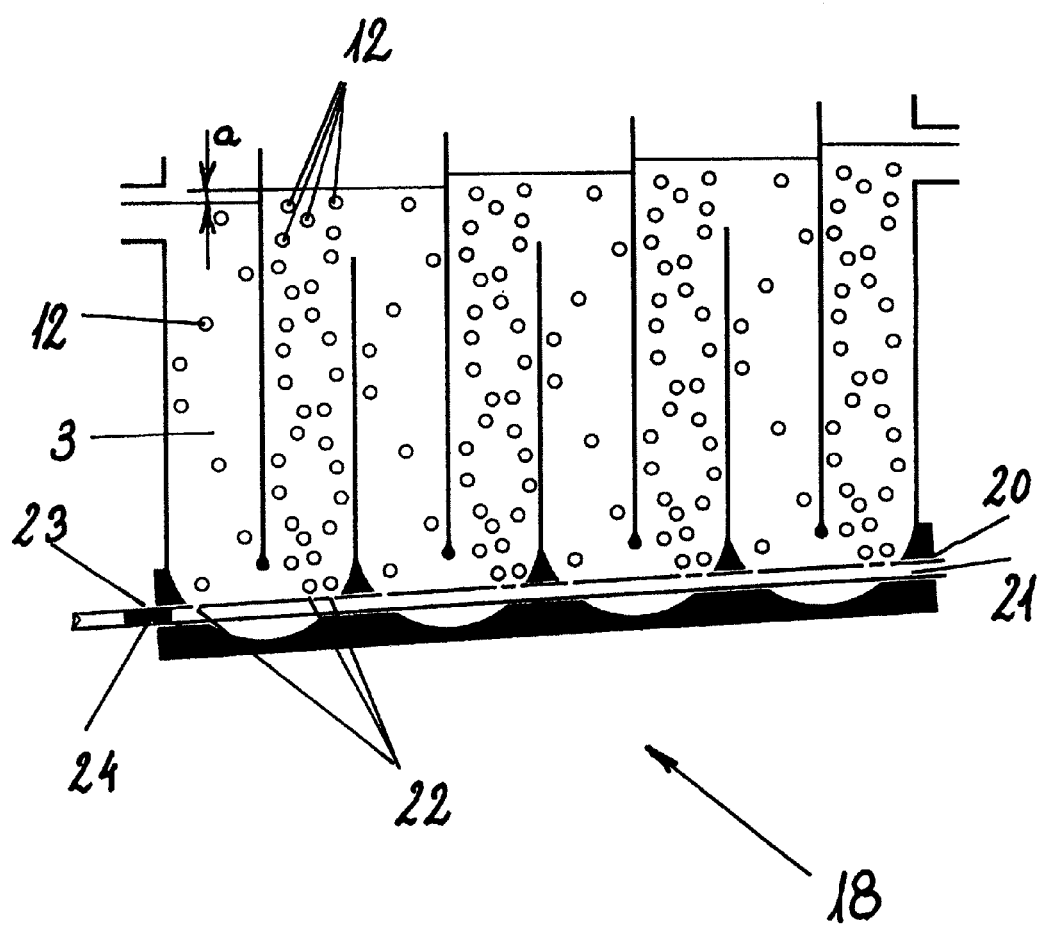
FIG. 8 shows a schematic diagram for the "gas lift" effect.

In accordance with FIGS. 1 to 3, a reactor, in particular, a biosolar reactor 1, comprises at least one reactor element 2, which is formed by two perpendicular pipes 3 connected at the bottom. An inlet 4 and an outlet 5 are provided at the upper reactor edge. For the assembly of a biosolar reactor 1, a multitude of reactor elements 2 are connected in series, whereby an outlet 5 is always connected with an inlet 4.

A biosolar reactor 1 of this type is used for a photochemical process, such as a photocatalytic and/or photosynthetic process, wherein, in particular, it is used for a breeding and production or hydrocultivation of preferably phototrophic microorganisms. For operation thereof, the biosolar reactor 1 is filled with a reaction medium 6, for example an aqueous solution or a suspension. During operation, the biosolar reactor 1 is only fed via its first inlet 4. The conductance or direction of flow of the reaction medium 6 is carried out upright, preferably perpendicularly, once from the top down and from the bottom up in a reactor element 2. If multiple interconnected reactor elements 2 are connected in series, the reaction medium 6 flows through the reactor in a meander-shaped way. Both the introduction and removal of the reaction medium 6 into and from the biosolar reactor 1 are preferably carried out continuously, without pressure and freely to the atmosphere via the upper reaction medium surface or closely above the upper liquid level or in the area of the upper liquid level.

The reactor elements 2 are thus connected with each other in a meander-shaped way as interconnected pipes 3, whereby the inlet 4 and the outlet 5 are positioned at the top. The reactor elements 2 are completely or partially open towards the top, depending on need.

Due to the hydrostatic pressure compensation and levelling, a flow of the reaction medium 6 is produced by feeding reaction medium 6 at the inlet 4. For the method, this means that a flow of the reaction medium 6 that is stress-free for the microorganisms is produced. This way, a free flow is enabled between the individual reactor elements 2 without having to supply any additional energy.

The reaction medium 6 moves through the reactor like a meander with a minimal loss of height in the liquid's effort to compensate the difference in level between the inlet 4 and the outlet 5.

An alternative design for a biosolar reactor 1 is shown in accordance with FIGS. 4 to 6. This biosolar reactor 1 comprises web plates or multiple web plates 7. In the case of this design, a reactor element 2 comprises two preferably rectangular, perpendicular chambers 8 formed by the web plates or multiple web plates 7, which is formed by a dividing wall 9 that is open at the bottom. Both the inlet 4 for introduction and the outlet 5 are provided at the upper reactor edge. Two reactor elements 2 are connected already in the exemplary embodiment shown in accordance with FIG. 4.

If two or more reactor elements 2 are connected, their dividing wall 10 is designed lower than the dividing wall 9 between the pipes 3 or chambers 8 of a reactor element 2. As a result, an overflow or interconnected opening is created when the liquid level in the reactor elements 2 is higher than the dividing wall 10 between the reactor elements 12. This way, the energy consumption is minimised due to the fact that pumps can largely be omitted between the process steps and a random number of equal or different process steps can be coupled with each other at the same flow level.

The individual reactor elements 2 can be designed transparent or translucent, or also light-proof, if required. Both glass or UV-transmittant plastic, such as e.g. polymethylmethacrylate, can be used as materials.

The biosolar reactor 1 is filled and operated in analogy to the designs ad FIG. 1 to 3.

With regard to incident light radiation onto the reactor elements 2, which is described in more detail later, an inclined reactor is shown in accordance with FIG. 6. Although the reactor is inclined at an angle A relative to a horizontal surface, the reaction medium 6 flows once from the top down or in the direction of gravity and from the bottom up or against the direction of gravity.

In accordance with FIG. 1 and FIG. 4, at least one introductory inlet 11, for example, a controllable valve, is provided at the bottom side of the reactor in the area of the diversion of the reactor medium 6 for continuous or batch-by-batch introduction of additives 12 (see FIG. 7), such as, for example, nutritive solutions or gasses and/or oxidising agents and/or active substances and/or dissolved substances or gasses promoting the process, preferably performed during the process.

In accordance with the method, the reaction medium 6 is optionally saturated with $CO_2$ or other gasses before entering into the reactor. The degree of saturation is concentrated in accordance with the requirements of the process and/or supplied with $CO_2$ or other gasses during the stay in the reactor.

The decreasing level of $CO_2$ in the reaction medium 6 caused by steady growth of the microorganisms during the photosynthetic process can be compensated by continuous and/or paged introduction of $CO_2$.

The decreasing efficiency in the reaction medium caused by steady reaction during the photochemical process can be compensated by continuous and/or batch-by-batch introduction of additional active gasses.

By introducing the additives at the bottom end of the liquid column via the introductory inlets 11 in accordance with FIG. 7, the additives 12 are mixed thoroughly and distributed equally in the reaction medium 6.

The introduction of additives 12, such as fluids and gasses, also optimises the provision with light, as all molecules or phototrophic microorganisms are conducted sufficiently to the light-flooded light zone of the reactor element 2 near the outer wall, indicated by the arrows 13, due to the resulting turbulence in the reaction medium 6.

The introduction of fluids and gasses produces turbulence in the reaction medium 6, whereby another advantageous result takes effect, namely that a continuous cleaning of the inner reactor surface is caused by the ascent of the gas bubbles.

Furthermore, the reaction medium 6 can also be heated or cooled by defined introduction of fluids and gasses. The introduced additives 12 can thus be used for controlled temperature regulation of the reaction medium 6.

In accordance with FIG. 8, the liquid and/or gaseous substances or additives 12 are introduced at the bottom side in the area of the diversion of the reaction medium 6. In a special embodiment of the reactor, a larger quantity of liquid and/or gaseous substances or additives 12 is introduced in the area of the reaction medium 6 flowing from the bottom up or against the direction of gravity than in the area of the reaction medium 6 flowing from the top down or in the direction of gravity. This way, as mentioned already and in accordance with the operating process of a mammoth pump, the liquid level in the pipe 3 or chamber passed through from the bottom up is raised in comparison with the pipe 3 or chamber passed through from the top down in a kind of "gas lift effect". This difference in the liquid level a can lead to a rise of the liquid level at the end of the last pipe 3 or chamber in comparison with the first pipe 3 or chamber in the case of a multiple serial connection of reactor elements 2 and an increased introduction of gas into each ascending pipe 3, if the rise of the liquid level is taken into account in the design of the reactor. Despite this increased introduction of preferably gaseous additives 12, a stress-free transport of the microorganisms is enabled.

Figure 9:
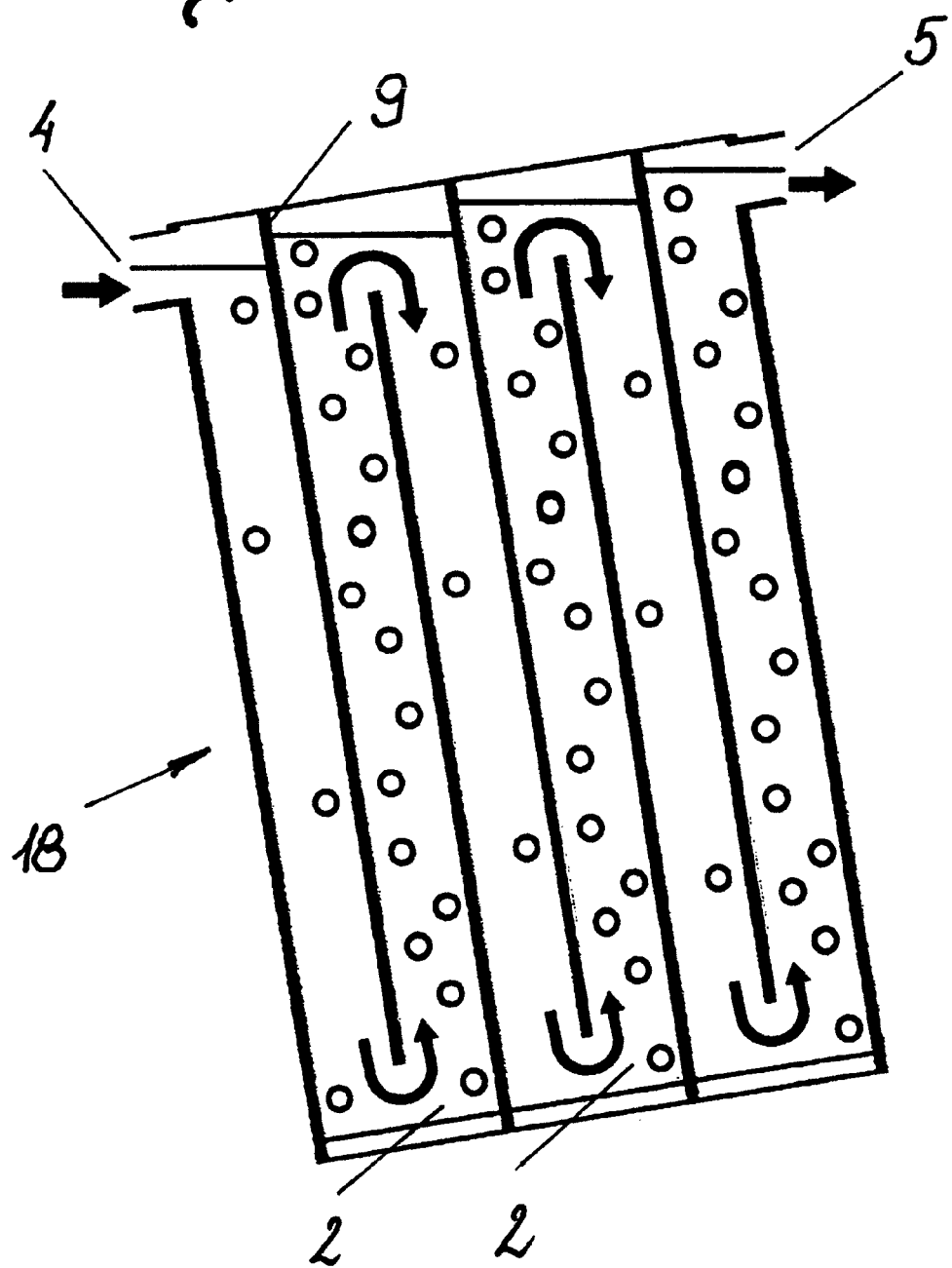
FIGS. 9 and 10 show schematic diagrams of applications of the "gas lift" effect.

In accordance with FIG. 9, this rise is taken into account in a reactor design with an equal structural design of reactor elements 2 connected in series, for example, if the elementary basis of the reactor rises to the same extent.

The positioning of reactor panels 18 at an angle along the panel axis provides the following advantage under application of the "gas lift effect":

The medium is introduced into a reactor panel 18 in the inlet opening 4, whereby the reactor panel is inclined at an angle along the panel axis, so that the inlet 4 is positioned lower than the outlet 5. Due to the "gas lift effect", which is effective in every second pipe of the reactor panel 18, a higher water column is created and the medium can flow into the next pipe despite the higher level and form interconnected vessels, thus rising.

The inclination is selected at a maximum angle that does not lead to a reverse overflow of the webs 9, which separate the two liquid columns inside a reactor element 2.

If the maximum possible angle were exceeded, the medium would flow back into the pipe out of which it came over the web 9 after passing the pipe 3, in which it flows against the force of gravity, thus producing a closed cycle with gas lift circulation.

By varying the inclination of the reactor panel 18 and the gas pressure or gas quantity, the desired gradient of the "gas lift effect" be regulated, whereby a control of the flow rate results with an increasing level of the upper edge of the liquid.

Figure 10:
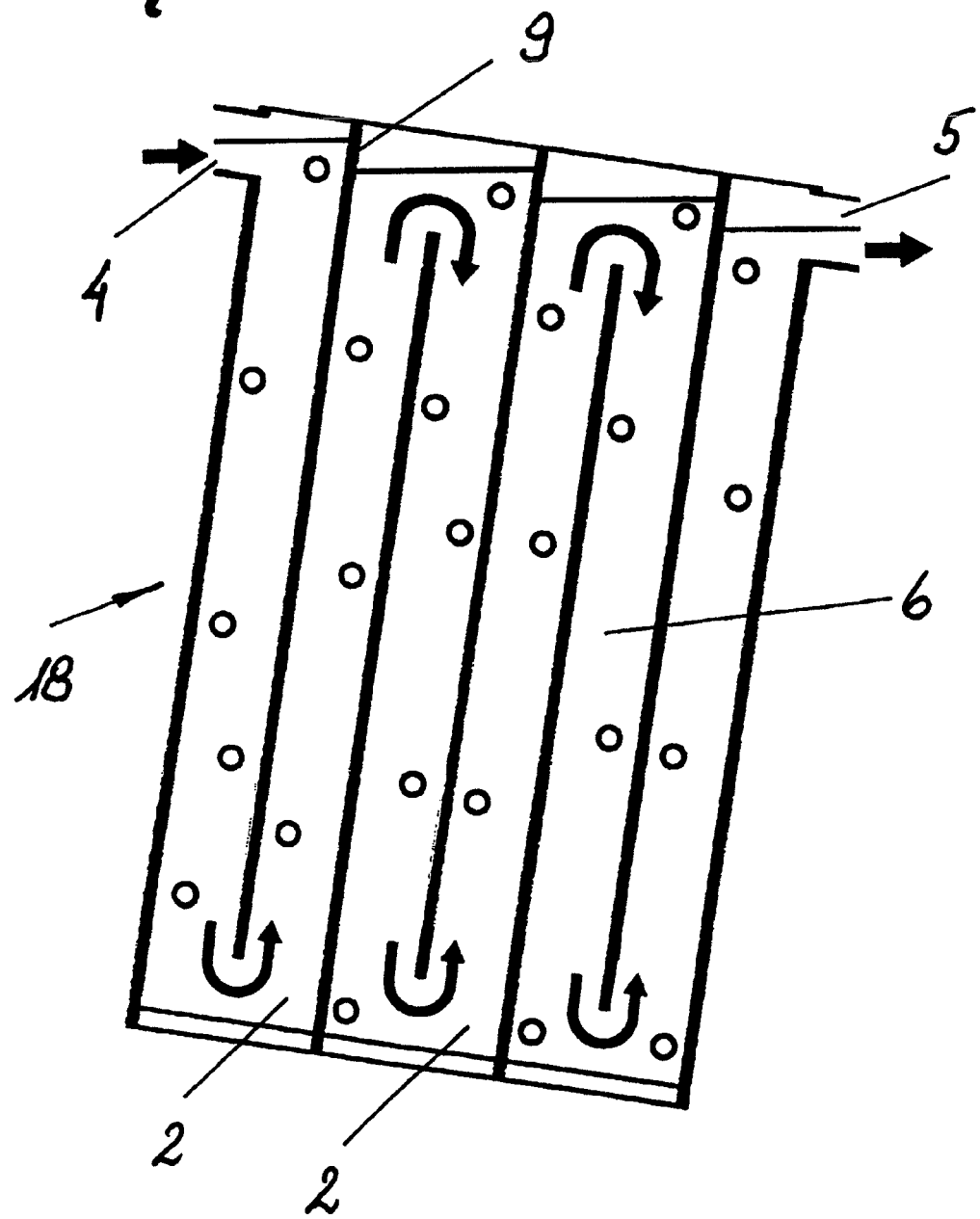

In another embodiment shown in FIG. 10, the flow rate can also be controlled by inclination at an angle, if no "gas lift effect" occurs due to little or no entry of gas.

The reaction medium 6 is introduced into a reactor panel 18 in the inlet 4, whereby the reactor panel is inclined at an angle along the panel axis, so that the inlet 4 is positioned higher than the outlet 5.

The hydrostatic compensation of levels is thus still effective between the individual reactor elements 2, however a small gradient is created respectively within the individual reactor elements 2 of a reactor panel 18, which has an acceleratory effect on the flow rate through the reactor panel 18.

The inclination can be selected at a maximum angle that does not result in an overflow of the webs 9 separating the liquid columns inside a reactor element 2 in the direction of the inlet 4 to the outlet 5, as in this case no flow is produced in the pipes 3, but the medium would only flow over the webs 9 further up and the medium in the reactor elements 2 would come to a standstill.

By varying the inclination of the reactor panel 18 and the gas pressure/gas quantity, the desired gradient can be regulated, whereby a control of the flow rate results with a decreasing level of the upper edge of the liquid.

Thus, the "gas lift effect" could be used by way of the examples listed below:

Use of the rise of the upper water edge:
additional height for settlement tanks;
additional height in order to overcome flow paths in between reactors or between process steps;
operation of a hydrocyclone by water running down;
passing through filters;
separation of products from the reaction medium;
passing through recycling systems for reutilisation of the medium; and
without using additional energy for pumps within the entire system Use of the invariability of the upper water edge:
no loss of height to be overcome in this phase of the process;
good control of the flow rate; and
moderate turbulence (provision with light and prophylaxis of film formation) and economic operation, if momentarily little gas is required in the process Use of the minor lowering of the upper water edge:
no major loss of height to be overcome in this phase of the process (downstream gas lift);
good control of the flow rate; and
minimum gassing required for turbulence (provision with light and prophylaxis of film formation) and thus economic operation, if momentarily little gas is required in the process The objective is to control the entire system in such a way that no additional energy must be used for the flow of the medium within the entire system, except for the gas lift at an economically reasonable position.

For the introduction of additives 12 in the area of the diversion in the reactor element 2 and/or in the reactor panel 18, bored holes 20 are provided for the arrangement of a preferably continuous pipe, in particular a gas pipe 21 with micro-boreholes 22 (see FIG. 8).

For an increased introduction of the gaseous additives 12, the gas pipe 21 is provided with a larger number of micro-boreholes 22 and/or micro-boreholes with a larger diameter in the area of the reaction medium 6 flowing from the bottom up or against the direction of gravity than in the area of the reaction medium 6 flowing from the top down or in the direction of gravity.

In order to facilitate quick replacement of the gas pipe 21 (FIG. 8), it the pipe 21 is provided with an outer and/or inner thread 23 at both ends. The gas pipes 21, for example, are designed in such a way that these can close off with the assembly gastight by way of a union nut. At least one of these union nuts is provided with a connection for a gas line.

In addition, the gas pipe 21 can be provided with a connecting piece 24 via its inner thread, which in turn can be screwed onto another gas pipe 21.

For replacement, the union nut is screwed off at one side, the connecting piece 24 is attached, and the new gas pipe 21 is attached to the other end of the connecting piece 24. Using the new gas pipe 21, the gas pipe 21 to be replaced is pushed through the assembly and simultaneously takes up its position thereby. This way, it is ensured that the gas pipe 21 to be replaced is pushed through the assembly under a minimal loss of gas or loss of liquid using the new gas pipe 21. This design permits maintenance or modification of the gas inlet unit without operational interruption or only minimal impairment of the process.

Figure 11:
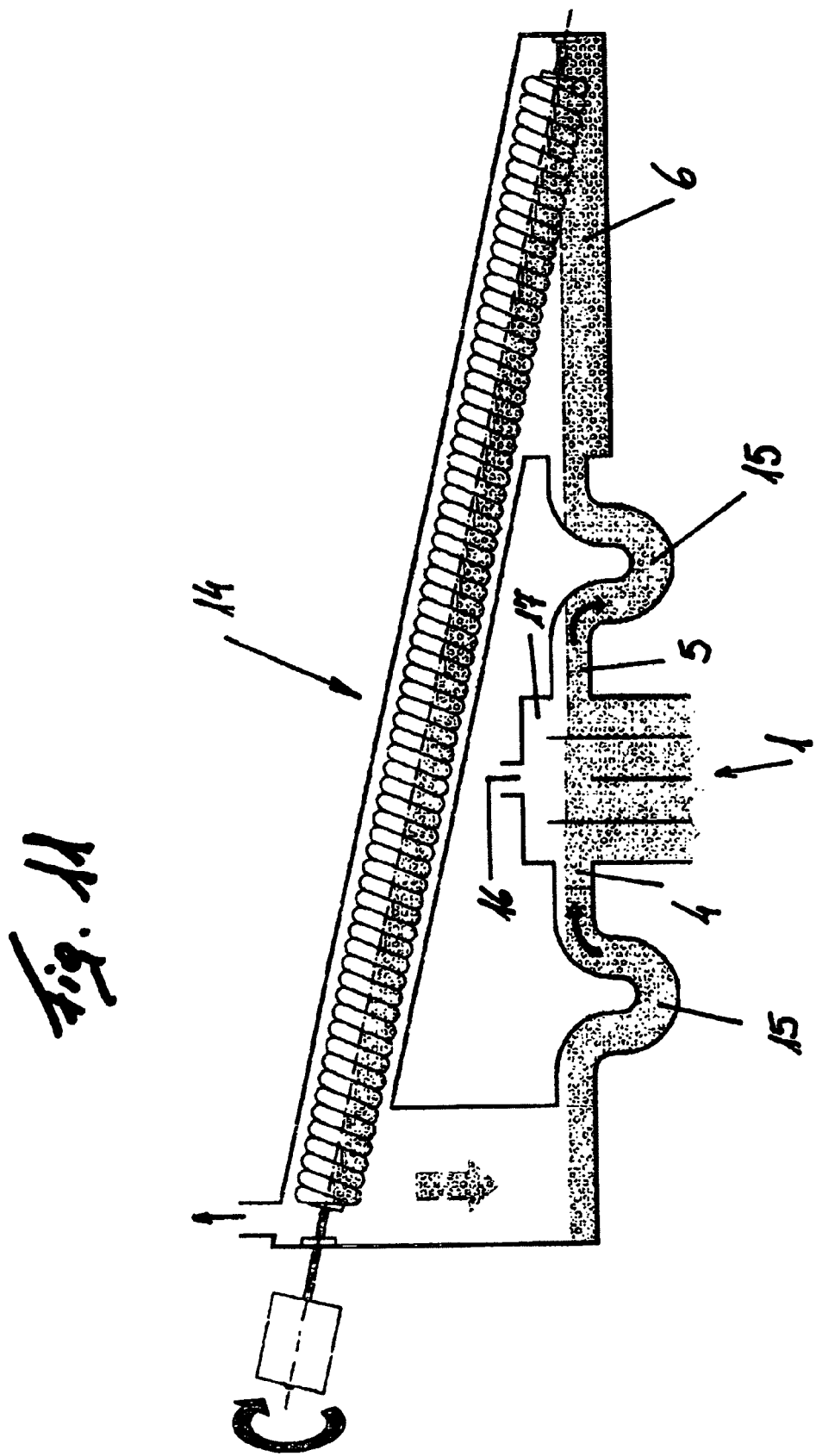
FIG. 11 shows a bioreactor with an Archimedian screw.

As an alternative or additional option to the "gas lift" explained above, the biosolar reactor 1 can be provided with an Archimedian screw 14 in accordance with FIG. 11. The Archimedian screw 14 or a spiral of Da Vinci serves for transport of the reaction medium 6 both inside the reactor as well as between reactor elements or reactors. A siphon 15 is provided respectively before the inlet 4 and after the outlet 5.

Naturally, the siphons 15 can also be positioned before the inlet 4 or after the outlet 5 from the reactor independently from the Archimedian screw 14. The reaction medium 6 can be conducted to the first reactor element 2 pressure-free or without pressure through a siphon 15.

The Archimedian screw 14 or a spiral of Da Vinci is used preferably in the method for continuous photocatalytic and photosynthetic processes and transports in biosolar reactors 1. In particular, if the transport of the reaction medium 6 demands that level differences are overcome. Single or also multiple stress-free transport is achieved using the Archimedian screw 14 or the spiral of Da Vinci. This device could be used for the following applications:

- transport, for multiple passing of the reaction medium 6 through the same reactor;
- transport between a series of possibly different reactors and/or maturation tanks passed once or multiple times;
- single or multiple transportation of a reaction medium 6 alternatively between a tank and any kind of bioreactor; and
- single or multiple transport of a reaction medium between tanks.

As already mentioned briefly, a maturation tank (not shown) for a, in particular, continuous photochemical or photosynthetic process can be provided after and/or before the biosolar reactor 1. The hydrostatic maturation tank is provided with meander-shaped reactor elements 2 of a similar design as the hydrostatic bioreactor, which enable a perpendicular flow. The maturation tank can be made of light-proof material, as phototrophic microorganisms only require the right temperature, nutrients and a possibility to discharge residues of metabolism in the resting phase. Moreover, a larger cross-section in proportion to the bioreactor can be used in the reactor elements 2, in order to regulate the resting time and to save space.

The desired and largely pressure-free or non-pressurised transport of the reaction medium 6 is achieved as follows: During the entire transport, the reaction medium 6 is not subjected to any other pressure than that created inside of the transport element due to the own weight of the reaction medium 6. The reaction medium 6 is not subjected to any centrifugal forces worth mentioning due to a minor speed of rotation. The development of the microorganisms or the progress of the process is not interrupted or disturbed by the transport. The pressure-free condition remains ensured by the use of the hydrostatic pressure compensation in an "Archimedian screw" or in a spiral of Da Vinci. The processes can be performed free from stress, acceleration and pressure.

During the entire transport, the reaction medium 6 is not subjected to any higher appression than that created inside of the transport element due to the free flow of the reaction medium. The development of the microorganisms or the progress of the process is not interrupted or disturbed by the transport. Abrasive injuries and damage to the cell walls of the microorganisms or molecules, such as by pumps, are ruled out.

The appression-free condition remains ensured by the use of the hydrostatic pressure compensation in an Archimedian screw or in a spiral of Da Vinci. For the removal of gaseous process products preferably carried out during the process, such as oxygen, for example, a removal outlet 16 is provided, which is provided above the reaction medium surface or above the upper side of the reactor elements. For the removal of these gaseous process products, a collecting device 17 with the removal outlet 16 provided above the liquid level of the reaction medium 6 or above the upper side of the reactor elements can be provided.

Figure 12:
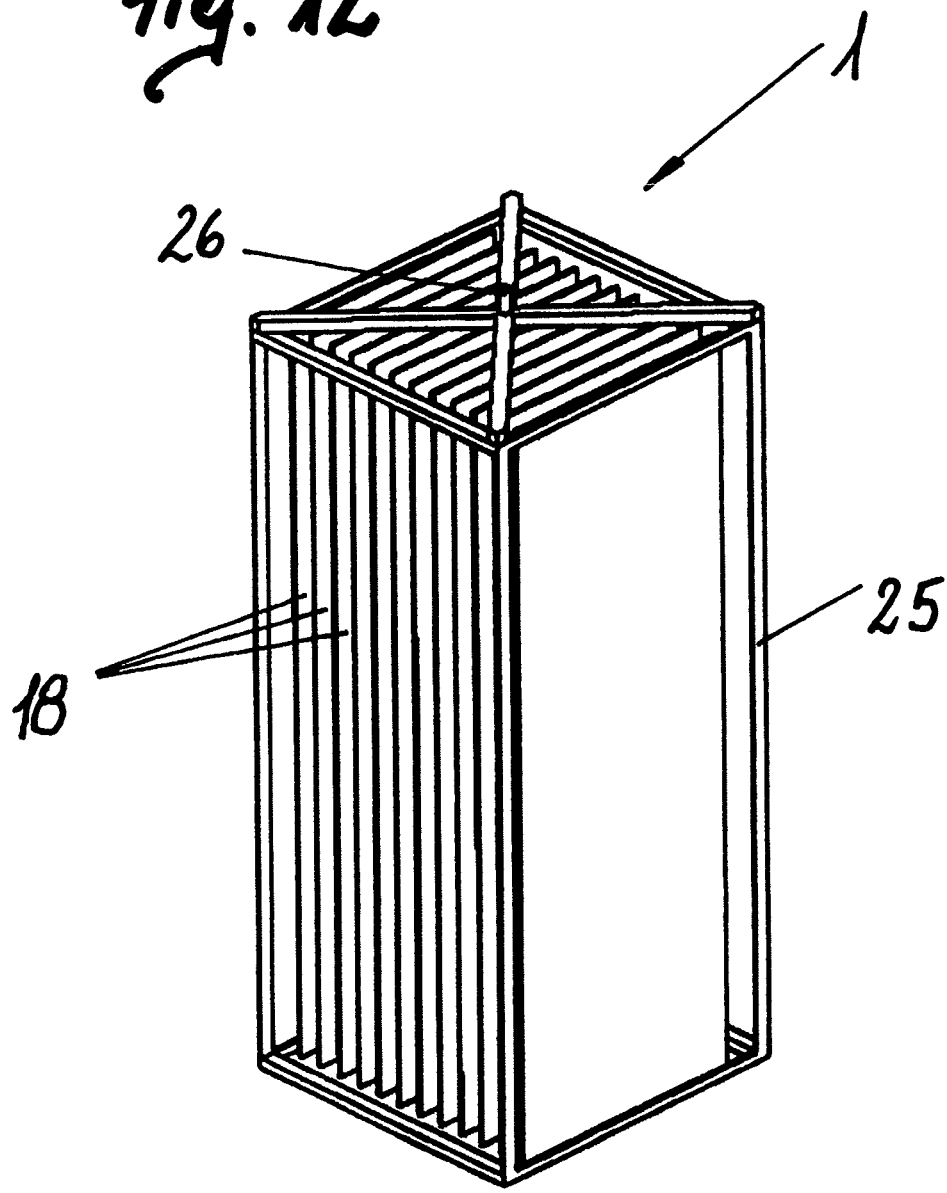
FIG. 12 shows a biosolar reactor.

In accordance with FIG. 12, the biosolar reactor 1 can be designed adjustable to the incident light radiation. In the case of poor solar irradiance, a bad geographical location, or in the case of phototrophic microorganisms or photocatalytic processes particularly in the need of light, the biosolar reactor 1 is guided or controlled in a revolving manner across the entire arch of the horizontal solar path in conformity with the solar irradiance.

The reactor panels 18 preferably connected with each other in series are arranged into a reactor, nearly in parallel to each other and preferably mounted firmly in a frame-like holding device 25. The biosolar reactor 1 is adjustable in relation to the incident light radiation via at least one preferably vertical axis 26 using a turning device, whereby the reactor can be provided, in particular standing, suspended or swimming, on a float.

To record the solar path, a sensor can be provided, or the use of data related to coordinates, time and date, via which the rotary movement for incident light radiation for the reactor is controlled.

As a matter of form, it must be noted that the incident light radiation for the reactor may also be carried out through artificial lighting.

In a system consisting of multiple reactors, the rotary movements for incident light radiation can be synchronised preferably for all reactors.

For better utilisation of the light rays, at least parts, in particular outer surfaces, of the reactor panels 18 and/or the reactor can also be designed reflecting light.

In accordance with FIG. 13, a reactor panel 18 formed by or of reactor elements 2 is arranged in such a way that the light or solar rays 19 indicated schematically impinge at an approximately right angle to the panel axis.

In accordance with FIG. 14, multiple reactor panels 18 preferably connected with each other are provided and arranged in such a way that the light or solar rays 19 run nearly in parallel to the axles of the solar panels.

In a special design variant, the reactor panels 18 are placed suspended and/or standing upright in an upper and/or lower holder or in the holding device 25.

This holder or holding device 25 can fulfil the following functions:

- the function as turning element, to follow the solar irradiance;
- to lift or lower the reactor in relation to other parts of the overall system;
- the tilting function, to tilt the reactor towards the sun;
- to serve as support for the reactor panels 18;
- to connect the reactor panels 18 in a meander-shaped way;
- to be able to seal the individual reactor elements gastight; and
- to tilt at least one reactor panel 18 at an angle along the panel axis.

This holder can take up at least two to any number of reactor panels 18 for a reactor.

This enables a close positioning and/or consecutive positioning of reactors, which permits a maximum utilisation of space.

The method enables an optimum combination of reactor phases under light and resting phases in the dark, as well as a stress-free transport.

This way, a setup of continuous single-cycle processes or modular, controlled, multiple passing through of individual parts is enabled.

Prior to the actual reaction, the reaction medium 6 can be supplied basically with nutrients and nutritive gasses that support the bioreaction from the start in an enrichment tank. In the case of wastewater treatment or pollutant elimination, a maximum initial enrichment that is reasonable for the phototrophic microorganisms can be produced in the reaction medium using the relevant pollutants.

The reaction medium 6 can be ideally temperature-controlled and the relevant phototrophic microorganisms or chemical substances for the purpose of the reaction can be introduced at a defined quantity.

The temperature, the process fluid content, the process gas content, the circulation, thorough mixing, the provision with light, and a discharge of the products of metabolism can be controlled and regulated in the reaction medium 6 in order to maintain the ideal reaction conditions.

The method described above solves the following problems in an advantageous manner:
- continuous photocatalytic and photosynthetic processes and transports in solar reactors;
- controlled and optimised energy consumption in the process;
- controlled and optimised introduction of nutritive solutions and solutions promoting the process;
- controlled and optimised introduction of nutritive gasses and process gasses;
- controlled and optimised reduction of pollutants;
- optimised removal and collection of gaseous process products;
- controlled and optimised provision with light;
- minimised use of space by light guidance;
- controlled and optimised process temperature;
- stress-free transport of the microorganisms in the reaction medium 6; and
- control of the flow rate.

The invention claimed is:

1. A photochemical process adapted to breed, produce, or hydrocultivate microorganisms, the process comprising:
conveying a reaction medium in a reactor having at least one reactor element that includes an inlet and an outlet at an upper reactor edge, two parallel chambers in fluid communication at a bottom of the chambers, and the inlet being coupled to one of the two parallel chambers and the outlet being coupled to the other of the two parallel chambers, such that the reaction medium is conveyed in the reactor in a meander-shaped way that includes moving the reaction medium along a direction that is perpendicular to or inclined at an angle to an imaginary horizontal plane, wherein, during the conveying, the reaction medium:
moves in the reactor at least once along a first direction defined as one of a top down direction and a direction of gravity; and
moves in the reactor at least once along a second direction defined as one of a bottom up direction and against the direction of gravity;
and
introducing into and removing from the reactor the reaction medium in a continuous manner without pressure and freely under atmospheric pressure and while exposed to the atmosphere.

2. The photochemical process of claim 1, wherein an upper surface of the reaction medium in the reactor is exposed to the atmosphere, and wherein the process produces hydrostatic pressure compensation and a leveling flow of the reaction medium.

3. The photochemical process of claim 1, wherein the photochemical process is at least one of a photocatalytic process and a photosynthetic process.

4. The photochemical process of claim 1, wherein the microorganisms comprise phototrophic microorganisms and the reactor is a bioreactor.

5. The photochemical process of claim 1, wherein the reaction medium is one of an aqueous solution and a suspension.

6. The photochemical process of claim 1, further comprising one of:
continuously introducing additives into the reaction medium;
batch-by-batch introducing additives into the reaction medium;
introducing additives to a bottom area of the reactor; and
introducing additives to a bottom area of the reactor in a manner which promotes diffusion.

7. The photochemical process of claim 6, wherein the additives comprising one of:
liquid additives;
gaseous additives;
nutritive solutions;
oxidising agents;
active substances; and
dissolved substances.

8. The photochemical process of claim 1, further comprising introducing additives into the reaction medium at a bottom end of a liquid column so that the additives are mixed thoroughly and distributed equally in the reaction medium.

9. The photochemical process of claim 1, further comprising introducing additives into the reaction medium at a known temperature.

10. The photochemical process of claim 1, further comprising introducing additives into the reaction medium at a location wherein the reaction medium diverges, wherein a larger quantity of the additives flows along the second direction than the first direction.

11. The photochemical process of claim 1, further comprising one of:
removing gaseous process products;
removing oxygen; and
removing gaseous process products from a reaction medium surface.

12. The photochemical process of claim 1, further comprising one of:
moving the reactor along an arcuate horizontal solar path;
guiding the reactor along an arcuate horizontal solar path;
controlling a movement of the reactor along an arcuate horizontal solar path; and
moving the reactor along an arcuate path that allows the reactor to receive solar irradiance.

13. The photochemical process of claim 1, further comprising,
during the conveying, conveying the reaction medium in the at least one reactor element, wherein the chambers are formed by two perpendicular pipes.

14. The photochemical process of claim 1, further comprising,
during the conveying, conveying the reaction medium between the chambers, which is formed by at least a dividing wall.

15. The photochemical process of claim 1, wherein the at least one reactor element comprises reactor elements further comprising one of:
utilizing one of an overflow and interconnected opening one of:
between reactor elements; and
at a location higher than a dividing wall between reactor elements.

16. The photochemical process of claim 1, further comprising one of:
  connecting reactor panels with each other;
  connecting reactor panels in series with each other;
  arranging reactor panels parallel to each other in the reactor;
  arranging reactor panels in a frame-like holding device; and
  arranging reactor panels in a frame-like holding device having at least one vertical axis that allows for movement of the reactor in relation to incident light radiation.

17. The photochemical process of claim 1, further comprising recording with a sensor a solar path and controlling movement of the reactor.

18. The photochemical process of claim 1, further comprising exposing the reactor to incident light radiation in the form of artificial light.

19. The photochemical process of claim 1, wherein the at least one reactor element comprises multiple reactor elements attached in series, and the method further comprises exposing the multiple reactor elements to incident light radiation.

20. The photochemical process of claim 1, further comprising one of:
  exposing reflective surfaces of the reactor to incident light radiation; and
  exposing outer surfaces of the reactor to incident light radiation.

21. A reactor for performing the photochemical process of claim 1, the device comprising:
  at least one reactor element having two parallel chambers in fluid communication at a bottom of the chambers and having an inlet and an outlet structured and arranged at an upper reactor edge to continuously introduce a reaction medium into and remove the reaction medium from the at least one reactor element one of freely under atmospheric pressure and while exposed to the atmosphere;
  a conveyor path structured and arranged to convey the reaction medium in the at least one reactor element in a meander-shaped way that includes moving the reaction medium along a direction that is perpendicular to or inclined at an angle to an imaginary horizontal plane; and
  at least one introductory inlet located at a location at which the reaction medium transitions between the first direction and the second direction, the at least one introductory inlet being coupled to an additive supply to selectively introduce additives into the reaction medium,
  wherein, in the conveyor, the reaction medium moves in the at least one reactor element:
    at least once along the first direction defined as one of a top down direction and a direction of gravity; and
    at least once along the second direction defined as one of a bottom up direction and against the direction of gravity.

22. A device for performing a photochemical process, comprising:
  an inlet and an outlet structured and arranged to continuously introduce a reaction medium into and remove the reaction medium from a reactor one of freely under atmospheric pressure and while exposed to the atmosphere, the reactor comprising a first chamber coupled to the inlet and a second chamber parallel to the first chamber coupled to the outlet;
  the reactor being structured and arranged to convey the reaction medium in a meander-shaped way, in which the reaction medium in at least one diversion area is diverted from, with respect to gravity, a downward flow to an upward flow, and being oriented to move the reaction medium along a direction perpendicular to or inclined at an angle to an imaginary horizontal plane; and
  at least one introductory inlet being located in the reactor and being coupled to an additive supply to introduce additives into the reaction medium to promote the photochemical process,
  wherein, in the reactor, the reaction medium moves:
    at least once along a first direction defined as one of a top down direction and a direction of gravity; and
    at least once along a second direction defined as one of a bottom up direction and against the direction of gravity.

23. The device of claim 22, wherein the at least one introductory inlet is structured and arranged to one of:
  continuously introduce the additives into the reaction medium;
  batch-by-batch introduce the additives into the reaction medium;
  introduce the additives to the at least one diversion area of the reactor; and
  introduce the additives to the at least one diversion area of the reactor in a manner which promotes diffusion.

24. The device of claim 22, wherein the additives comprise at least one of:
  liquid additives;
  gaseous additives;
  nutritive solutions;
  oxidising agents;
  active substances; and
  dissolved substances.

25. The device of claim 22, wherein the at least one introductory inlet is structured and arranged to introduce additives into the reaction medium at a bottom end of a liquid column so that the additives are mixed thoroughly and distributed equally in the reaction medium.

26. The device of claim 22, wherein the at least one introductory inlet is structured and arranged as at least one of bored holes, micro-boreholes, inner threads and outer threads.

27. The device of claim 22, wherein the at least one introductory inlet comprises a pipe for introducing the additives into the reaction medium comprising at least one of bored holes, micro-boreholes, inner threads and outer threads.

28. The device of claim 22, further comprising a collecting device for collecting gas having a removal outlet arranged above one of a surface of the reaction medium and an upper side of the reactor.

29. A device comprising:
  an arrangement structured and arranged to continuously introduce into and remove from a reactor a reaction medium; and
  a conveying arrangement structured and arranged to convey a reaction medium in the reactor in a meander-shaped way that includes moving the reaction medium along a direction that perpendicularly or inclined at an angle to an imaginary horizontal plane,
  wherein, during the conveying, the reaction medium moves in the reactor:
    at least once along a first direction defined as one of a top down direction and a direction of gravity;
    at least once along a second direction defined as one of a bottom up direction and against the direction of gravity;
    one of freely under atmospheric pressure and while exposed to the atmosphere; and at least one siphon arranged, with reference to a reactive medium flow direction, at least one of before the inlet and after the outlet.

30. A device comprising:

an arrangement structured and arranged to continuously introduce into and remove from a reactor a reaction medium; and a conveying arrangement structured and arranged to convey a reaction medium in the reactor in a meander-shaped way that includes moving the reaction medium along a direction that perpendicularly or inclined at an angle to an imaginary horizontal plane, wherein, during the conveying, the reaction medium moves in the reactor:
- at least once along a first direction defined as one of a top down direction and a direction of gravity;
- at least once along a second direction defined as one of a bottom up direction and against the direction of gravity;
- one of freely under atmospheric pressure and while exposed to the atmosphere; and
- one of an Archimedian screw and a spiral of Da Vinci arranged inside the reactor to transport the reaction medium within the conveyor.

31. A photochemical process adapted to breed, produce, or hydrocultivate microorganisms, the process comprising:

conveying a reaction medium in a reactor in a meander-shaped way that includes:
- moving the reaction medium in the reactor at least once along a first direction defined as one of a top down direction and a direction of gravity; and
- moving the reaction medium in the reactor at least once along a second direction defined as one of a bottom up direction and against the direction of gravity, wherein, during the conveying, the microorganisms move in a stress-free manner in the reactor one of freely under atmospheric pressure and while exposed to the atmosphere; and introducing $CO_2$ into the reaction medium one of before entering the reactor or within the reactor and additives into the reaction medium in at least one of a continuous and batch-by-batch manner to promote the microorganism process.

* * * * *